United States Patent [19]

Manautou et al.

[11]  3,968,011
[45]  *July 6, 1976

[54] TEST IMPLEMENT AND TEST METHOD FOR COLORIMETRICALLY DETERMINING WHETHER A FEMALE IS FERTILE OR PREGNANT

[75] Inventors: Jorge Martinez Manautou; Adolfo Rosado Garcia, both of Mexico City, Mexico

[73] Assignee: Alza Corporation, Palo Alto, Calif.

[ * ] Notice: The portion of the term of this patent subsequent to Apr. 1, 1992, has been disclaimed.

[22] Filed: Mar. 27, 1975

[21] Appl. No.: 562,743

Related U.S. Application Data

[63] Continuation-in-part of Ser. No. 333,029, Feb. 16, 1973, Pat. No. 3,875,013.

[52] U.S. Cl. ........................................ 195/103.5 R
[51] Int. Cl.² .................. G01N 31/14; G01N 33/16
[58] Field of Search ............................. 195/103.5 R

[56]         References Cited
          UNITED STATES PATENTS
3,699,005   10/1972   Foster .......................... 195/103.5 R
3,875,013   4/1975    Manautou et al. ............ 195/103.5 R

*Primary Examiner*—Alvin E. Tanenholtz
*Attorney, Agent, or Firm*—Thomas E. Ciotti; Paul L. Sabatine; Edward L. Mandell

[57]              ABSTRACT

A test implement and method for colorimetrically assaying the quantity of N-acetyl-β-glucosaminidase in a female biological medium, such as saliva, which quantity is indicia of fertility or pregnancy. The implement is an absorbent material, such as paper strip, impregnated with a phenolic derivative of N-acetyl-β-d-glucosamine that reacts in the presence of the glucosaminidase at an acid pH to form a phenol that has a distinct color at an alkaline pH, and a buffer that maintains said acid pH. The method may be carried out by wetting the implement with the medium, alowing the phenol to form, raising the pH to alkalinity by wetting the implement with an appropriate buffer solution, and comparing the color of the implement with a color standard.

17 Claims, 4 Drawing Figures

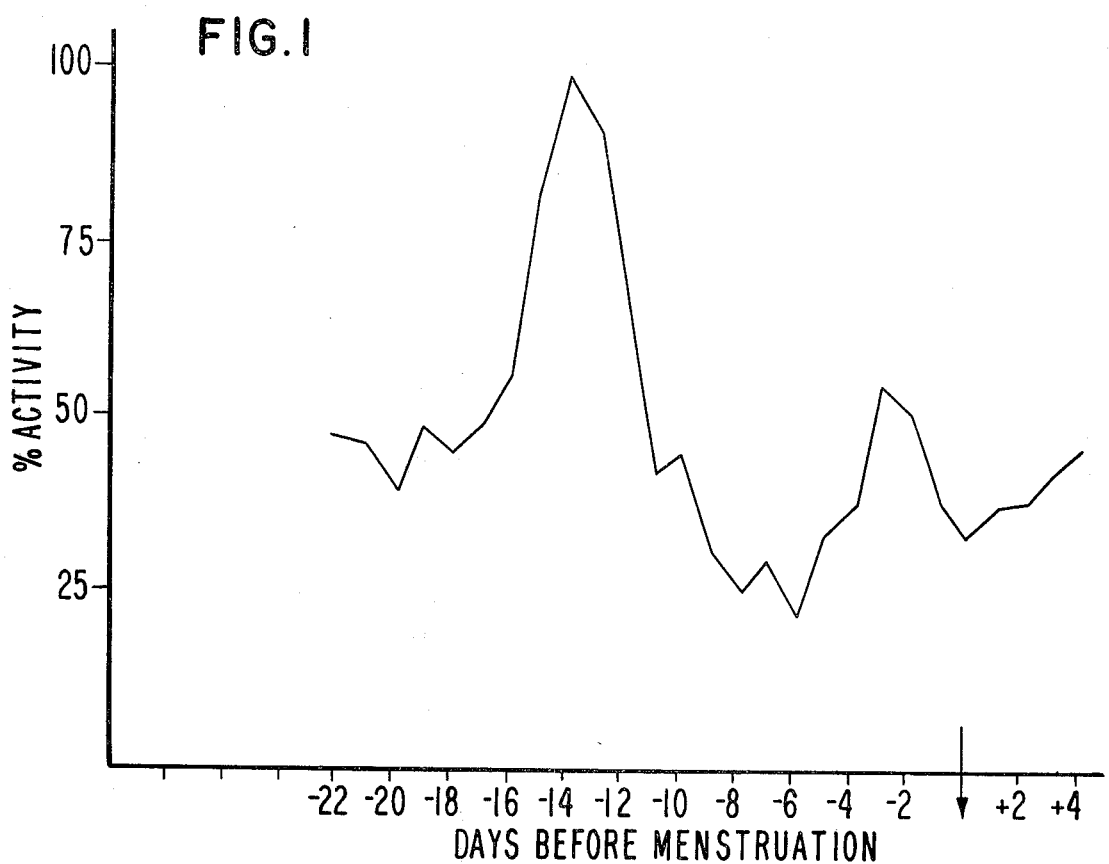
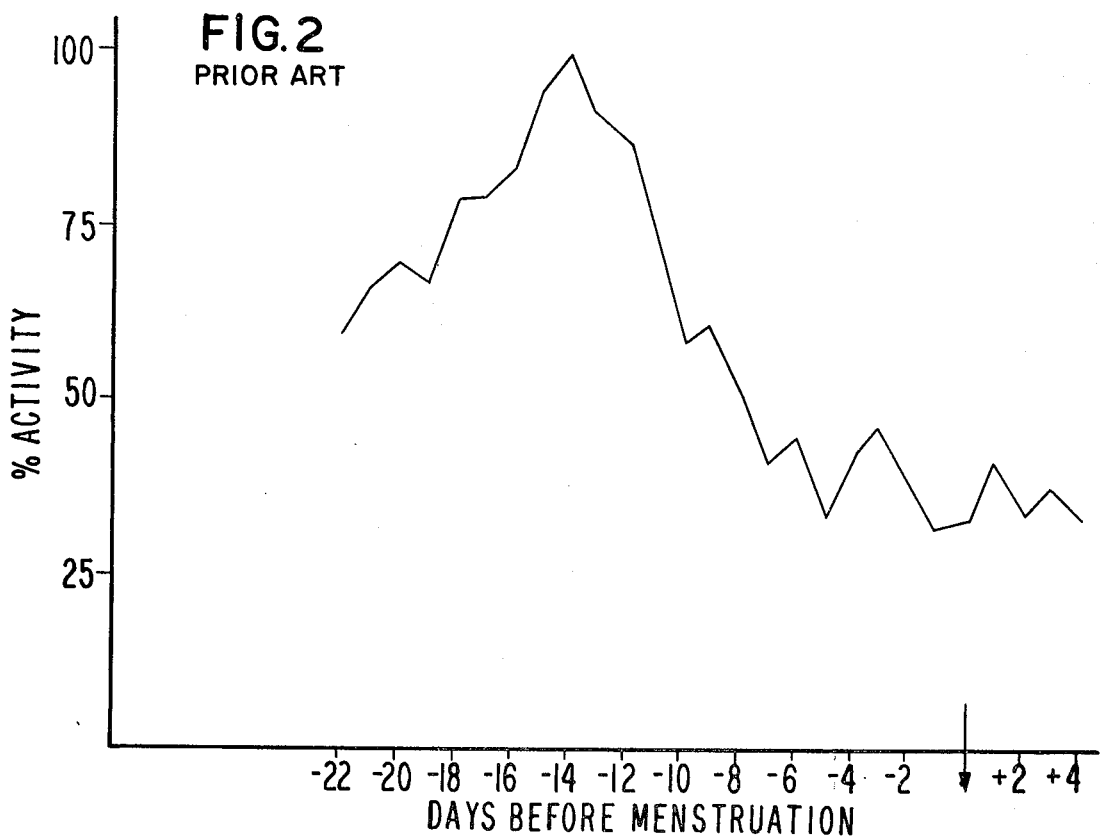

TEST IMPLEMENT AND TEST METHOD FOR COLORIMETRICALLY DETERMINING WHETHER A FEMALE IS FERTILE OR PREGNANT

CROSS-REFERENCE TO RELATED APPLICATIONS

This application is a continuation-in-part of application Ser. No. 333,029 filed February 16, 1973, issued April 1, 1975 as U.S. Pat. No. 3,875,013.

BACKGROUND OF THE INVENTION

1. Field of the Invention

The invention is an implement and a method for colorimetrically determining whether a woman is fertile or pregnant.

2. Description of the Prior Art

There is considerable interest in detecting the fertile period of women and also considerable interest in ascertaining whether a woman is pregnant in the early stages of gestation. This interest in detecting the fertile period is important to those women who desire to have an offspring, and also to those who wish to avoid having an offspring. The interest in detecting the presence of pregnancy is important to those who desire to provide medical care for the health of the female and the offspring and also for interrupting an unwanted pregnancy.

Test implements and methods for colorimetrically determining whether a woman is fertile are described in U.S. Pat. Nos. 3,406,016 and 3,699,005. Both patents describe test implements in the form of a strip of paper. In U.S. Pat. No. 3,406,016 the paper strip is impregnated with a peroxidase and guaiac. The strip changes color when wet with saliva if the woman is in her fertile period, the change being caused by the presence of peroxide in the saliva. In U.S. Pat. No. 3,699,005 the paper strip is impregnated with indoxyl phosphate or 5-bromoindoxyl phosphate and a nontoxic buffer that maintains a pH of 10.0–10.3. The strip changes color when wet with saliva if the woman is in her fertile period, with the color change being caused by increased levels of alkaline phosphatase in the saliva during the fertile period. Colorimetric assays for measuring acid phosphatases in biological liquids are known from U.S. Pat. No. 3,595,756.

SUMMARY OF THE INVENTION

The invention is based on the discovery that the quantity of N-acetyl-β-glucosaminidase in female biological fluids is indicia of fertility and pregnancy or the lack of same. Specifically it was discovered that there is a sharp increase in the amount of N-acetyl-β-glucosaminidase in such fluids during the fertile period of the menstrual cycle and that pregnancy is associated with a decrease in the amount of N-acetyl-β-glucosaminidase during a particular time period of the normal menstrual cycle.

One aspect of the invention is a test implement for colorimetrically determining the quantity of N-acetyl-β-glucosaminidase present in a female biological medium, said quantity being indicia of fertility or pregnancy, comprising an absorbent material containing a buffer that is capable of maintaining an acidic pH and an effective amount of an N-acetyl-β-d-glucosaminide that reacts in the presence of said glucosaminidase at said pH to form a reaction product that has a distinct color at a predetermined pH. The predetermined pH will usually be an alkaline pH.

A second aspect of the invention is a method for colorimetrically determining the quantity of N-acetyl-β-glucosaminidase present in a female biological medium, said quantity being indicia of fertility or pregnancy, comprising contacting said medium at an acid pH with an N-acetyl-β-d-glucosaminide that reacts in the presence of said glucosaminidase at said acidic pH to form a reaction product that has a distinct color at a predetermined pH and, after said reaction product has formed, establishing said predetermined pH. The predetermined pH will usually be an alkaline pH.

BRIEF DESCRIPTION OF THE DRAWINGS

In the drawings:

FIG. 1 is a graph illustrating the variation of the activity (quantity) of N-acetyl-β-glucosaminidase in female saliva during a portion of the menstrual cycle;

FIGS. 2 and 3 are graphs illustrating the variations in the activities (quantities) of alkaline phosphatase and acid phosphatase, respectively, in female saliva during a portion of the menstrual cycle. Such variations of alkaline phosphatase form the basis for U.S. Pat. No. 3,699,005.

Figure 3:
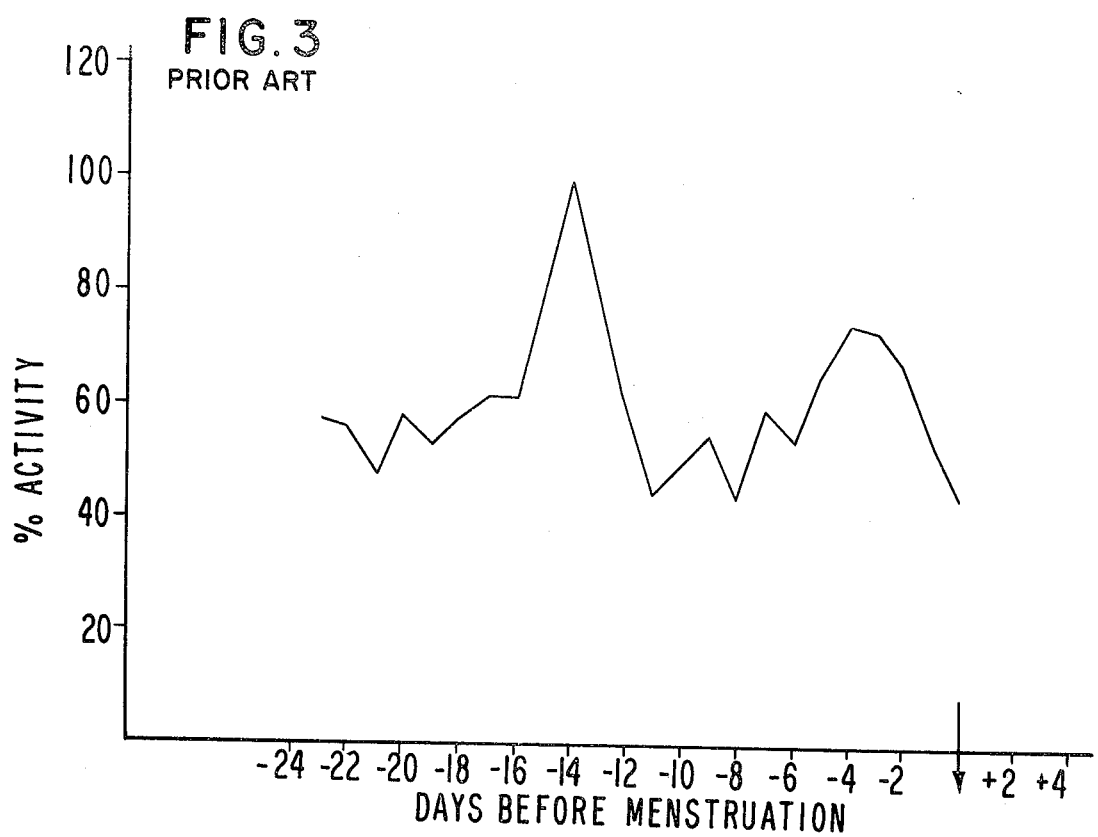

In each of FIGS. 1–3, the results have been normalized by ascribing a value of 100 to the highest enzymatic activity during the menstrual cycle. The arrow through zero (0) indicates the beginning of menstruation.

DETAILED DESCRIPTION OF THE INVENTION

The invention method involves colorimetrically assaying a biological fluid, such as saliva, vaginal fluid or cervical fluid, for N-acetyl-β-glucosaminidase with an N-acetyl-β-glucosaminide that reacts in the presence of said glucosaminidase at an acid pH to form a reaction product that has a distinct color at a predetermined pH, normally an alkaline pH. Such glucosaminides are derivatives of N-acetyl-β-d-glucosamine that have a substituent that is removed in the reaction and formed into said reaction product. Preferably the glucosaminide is a colorless or substantially colorless phenolic derivative of N-acetyl-β-d-glucosamine that reacts in the presence of said glucosaminidase at an acid pH to form a phenol that has a distinct color at an alkaline pH. In most instances reaction will occur at an acid pH of 4–5 and the distinct color will appear at an alkaline pH of 8–11, usually 9–11. As used herein the term "phenol" denotes aryl hydroxides generally rather than hydroxybenzene specifically. Examples of such phenolic derivatives are p-nitrophenyl-N-acetyl-β-d-glucosaminide, 1-(p-nitrocatechol)-N-acetyl-β-d-glucosaminide, 2-(p-nitrocatechol)-N-acetyl-β-d-glucosaminide, 3,3-bis(p-hydroxyphenyl)phthalid-N-acetyl-β-d-glucosaminide, 3-amino-4-nitrophenyl-N-acetyl-β-d-glucosaminide, 2-methyl-4-nitrophenyl-N-acetyl-β-d-glucosaminide, 3-methyl-4-nitrophenyl-N-acetyl-β-d-glucosaminide, 3-nitro-2,4,6-trimethylphenyl-N-acetyl-β-d-glucosaminide, 2-acetylamino-4-nitrophenyl-N-acetyl-β-d-glucosaminide, 3-nitro-4-methoxyphenyl-N-acetyl-β-d-glucosaminide, 3-nitro-4-acetylphenyl-N-acetyl-β-d-glucosaminide, 3-nitro-4-methylphenyl-N-acetyl-β-d- glucosaminide, 2-methoxy-4-nitrophenyl-N-acetyl-$\beta$-d-glucosaminide, m-nitrophenyl-N-acetyl-$\beta$-d-glucosaminide, 2,4-dinitrophenyl-N-acetyl-$\beta$-d-glucosaminide, 2,6-dinitrophenyl-N-acetyl-$\beta$-d-glucosaminide, 2,5-dinitrophenyl-N-acetyl-$\beta$-d-glucosaminide, o-nitrophenyl-N-acetyl-$\beta$-d-glucosaminide, and 2-amino-4-nitrophenyl-N-acetyl-$\beta$-d-glucosaminide. The amount of glucosaminide used in the method and implement should be sufficient to allow the formation of the maximum amount of said reaction product that is possible with the quantity of glucosaminidase present in the specimen being assayed during the given incubation (reaction) period. Such amounts are effective to produce a maximum color response from the quantity of glucosaminidase present in the specimen, with the intensity of the color being a measure of the quantity.

The method may be carried out in solution by first mixing a sample of a female fluid, such as 0.1 ml of saliva, with 0.1 ml of 0.1 M p-nitrophenyl-N-acetyl-$\beta$-d-glucosaminide dissolved in 0.1 M sodium citrate-citric acid buffer and 0.2 ml of 0.1 M sodium citrate buffer, pH 4.5. Then, after shaking until the reagents are mixed, the reagents are permitted to incubate for 30 minutes at room temperature, to allow the N-acetyl-$\beta$-glucosaminidase present in the saliva to hydrolytically act on the p-nitrophenyl-N-acetyl-$\beta$-d-glucosaminide to remove the p-nitrophenyl group therefrom and form p-nitrophenol. At the end of the incubation period, a second buffer consisting of 1.0 ml of 1.0 M sodium glycinate buffer, pH 10.3, is added to the reaction mixture to stop the hydrolytic activity and to develop the yellow color characteristic of p-nitrophenol at alkaline pH's. The absorbence of the reaction mixture is measured at 400 nm and compared to a standard absorbence curve prepared with solutions of known concentrations of p-nitrophenol at pH 10.3. In a similar manner other phenolic derivatives of N-acetyl-$\beta$-d-glucosamine may be used in the method. For instance 0.1 M 3,3-bis(p-hydroxyphenyl)phthalid-N-acetyl-$\beta$-d-glucosaminide may be substituted for p-nitrophenyl-N-acetyl-$\beta$-d-glucosaminide in the above described example. In that instance phenophthalein is the reaction product that is formed.

The method may also be carried out using the test implement of the invention. The implement comprises an absorbent material that contains an N-acetyl-$\beta$-d-glucosaminide as described above and a buffer that maintains an acid pH. Absorbent materials that may be used are those that by means of capillary action or any other physical chemical technique are able to hold liquids. Such materials include test paper, e.g., filter paper, cellulose strips, wood strips, felt, porous ceramic strips, velour and cloths. Paper is preferred because it is inexpensive. A typical test implement may be prepared by impregnating a strip of porous paper with 0.1 to 0.5 ml of buffered substrate consisting of 0.1 M p-nitrophenyl-N-acetyl-$\beta$-d-glucosaminide dissolved in 0.1 M sodium citrate buffer, pH 4–5. Then the strip is dried at temperatures between ambient and 100°C (without charring), to evaporate the aqueous solvent and leave the glucosaminide and buffer on the paper.

The test implement so prepared may be used to detect the fertility period as follows. The woman touches the implement to her tongue or otherwise wets the implement with her saliva and then waits about 20 to 40 minutes, usually 30 minutes, at ambient temperature for the phenol reaction product to form on the wetted portion of the strip. The phenol's color may then be developed by wetting the strip with a small amount of 0.1 M sodium glycinate buffer, pH 9–11. The strip is then compared to a standard color chart that has a series of color spots similarly developed from known concentrations of p-nitrophenol at pH 9–11. The test implement will develop a maximum color during the period of ovulation and fertility of the woman and it will undergo a minimum or no color change at other times. In relation to FIG. 1, the test implement would show a distinct color change in the period extending from about 18 to 11 days prior to menstruation in response to the illustrated sharp increase in glucosaminidase activity during that period. A woman may wish to be sexually active or inactive during that period in accordance with her desire to become pregnant.

The sensitivity of the invention method in relation to the methods based on increased phosphatase activity is illustrated by comparing FIG. 1 with FIGS. 2 and 3. The test results shown in FIG. 2 and 3 are determined as follows. The alkaline phosphatase test is performed by first preparing a 0.1 M sodium or potassium glycinate buffer adjusted to pH 9.6 and a buffered substrate comprised of 0.1 M p-nitrophenylphosphate dissolved in glycine buffer, 0.1 M, pH 9.6. The test is performed by adding 1.0 ml of buffered substrate mixture to 0.2 ml of saliva, with shaking and incubation for 45 minutes at 37°C. After this period of time, the color developed is measured at 400 nm, and compared to a standard p-nitrophenol color curve. The acid phosphates test is carried out by first preparing a 0.1 M acetic acid/sodium acetate buffer adjusted to pH 4.7, a buffered substrate comprised of p-nitrophenylphosphate disodium salt, 0.1 M, dissolved in 0.1 M sodium acetate buffer adjusted to pH 4.7, and lastly an 1.0 M sodium alkaline glycine buffer adjusted to pH 10.3. The test consists of adding 0.1 ml of the buffered substrate and 0.2 ml of the acid/acetate buffer to 0.1 ml of saliva, followed by shaking and incubation for 30 minutes at ambient temperature. At the end of this period, 1.0 ml of glycine buffer is added to the reaction mixture, and the mixture's absorbency is measured at 400 nm and compared to a standard p-nitrophenol color curve. As shown in FIGS. 1–3, the base level of glucosaminidase activity is usually well below 50 percent; whereas the base levels of acid phosphates and alkaline phosphatase activities are usually above 50 percent. This means that the increases in phosphatase activities associated with fertility are generally not as great as the corresponding increase in glucosaminidase activity and that the color change caused by the former may not be as distinct as the color change caused by the latter. Also, in the alkaline phosphatase test the increased activity spans a greater time period than does the increased glucosaminidase activity, indicating that the phosphatase test may not be as accurate as the glucosaminidase test.

Figure 4:
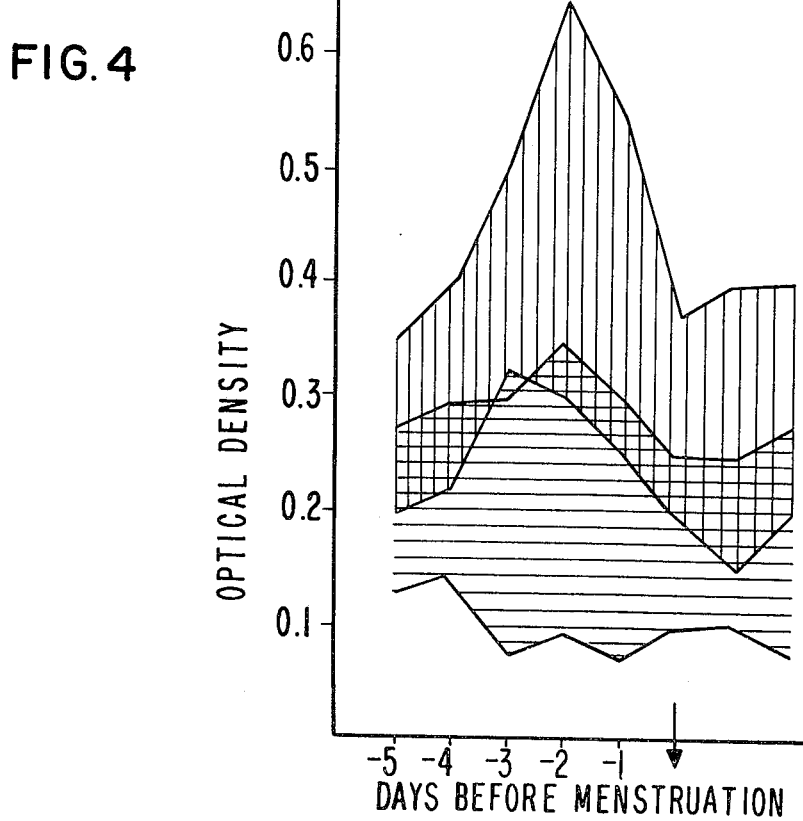
FIG. 4 illustrates the correlation between amounts of N-acetyl-β-glucosaminidase in female saliva if the woman is not pregnant and the amounts of same if pregnancy exists, during a particular portion of the normal menstrual cycle.

As depicted in FIG. 1 there is a smaller, second increase in glucosaminidase activity that occurs in the few days preceding the beginning of menstruation. FIG. 4 is an enlarged illustration of that second increase and the effect of pregnancy on it as determined by testing 40 nonpregnant women and 8 pregnant women in accordance with the invention. Glucosaminidase activity is reported as the normalized optical density of test solutions determined by their absorbencies at 400 nm. The arrow through zero (0) indicates the first day of menstruation for the nonpregnant women and the day menstruation would normally be expected to begin in the absence of pregnancy for the pregnant women. The vertically lined area is the optical density range exhibited by the nonpregnant women. The horizontally lined area is the optical density range exhibited by the pregnant women. As shown, pregnancy substantially eliminates the second increase in glucosaminidase activity and is generally associated with decreased activity during the test period. Accordingly, if a hypothetical woman's test falls in the area that is only horizontally lined, she is likely pregnant. If it falls in the area that is both horizontally and vertically lined, the test is inconclusive. And, if it falls in the area that is only vertically lined, she is probably not pregnant.

Modifications of the above described invention method and implement that are within the skill of the chemical, pharmaceutical and/or medical arts are intended to be within the scope of this invention.

We claim:

1. A test implement for colorimetrically determining the quantity of N-acetyl-β-glucosaminidase present in a female biological medium, said quantity being indicia of fertility or pregnancy, comprising an absorbent material containing a buffer that is capable of maintaining an acidic pH and an effective amount of an N-acetyl-β-d-glucosaminide that reacts in the presence of said glucosaminidase at said pH to form a reaction product that has a distinct color at a predetermined pH.

2. The test implement of claim 1 wherein the N-acetyl-β-d-glucosaminide is a phenolic derivative of N-acetyl-β-d-glucosamine that reacts with said glucosaminidase at said acidic pH to form a phenol that has a distinct color at an alkaline pH.

3. The test implement of claim 2 wherein said acidic pH is in the range of 4–5 and said alkaline pH is in the range of 8–11.

4. The test implement of claim 3 wherein said alkaline pH is in the range of 9–11.

5. The test implement of claim 2 wherein the phenolic derivative of N-acetyl-β-d-glucosamine is selected from the group consisting of 2-(p-nitrocatechol)-N-acetyl-β-d-glucosaminide, 3-amino-4-nitrophenyl-N-acetyl-β-d-glucosaminide, 2-methyl-4-nitrophenyl-N-acetyl-β-d-glucosaminide, 3-methyl-4-nitrophenyl-N-acetyl-β-d-glucosaminide, 3-nitro-2,4,6-trimethylphenyl-N-acetyl-β-d-glucosaminide, 2-acetylamino-4-nitrophenyl-N-acetyl-β-d-glucosaminide, 3-nitro-4-methoxyphenyl-N-acetyl-β-d-glucosaminide, 3-nitro-4-acetylphenyl-N-acetyl-β-N-glucosaminide, 3-nitro-4-methylphenyl-N-acetyl-β-d-glucosaminide, 2-methoxy-4-nitrophenyl-N-acetyl-β-d-glucosaminide, m-nitrophenyl-N-acetyl-β-d-glucosaminide, 2,4-dinitrophenyl-N-acetyl-β-d-glucosaminide, 2,6-dinitrophenyl-N-acetyl-β-d-glucosaminide, 2,5-dinitrophenyl-N-acetyl-β-d-glucosaminide, o-nitrophenyl-N-acetyl-β-d-glucosaminide, and 2-amino-4-nitrophenyl-N-acetyl-β-d-glucosaminide.

6. The test implement of claim 1 wherein the absorbent material is a strip of paper.

7. The test implement of claim 1 wherein the buffer is compounded from sodium citrate and citric acid.

8. The test implement of claim 1 wherein the absorbent material is a strip of paper, the buffer is compounded from sodium citrate and citric acid, the acidic pH is in the range of 4–5, the N-acetyl-β-d-glucosaminide is selected from the group consisting of p-nitrophenyl-N-acetyl-β-d-glucosaminide and 3,3-bis(p-hydroxyphenyl)phthalid-N-acetyl-β-d-glucosaminide, and said predetermined pH is in the range of 9–11.

9. A method for colorimetrically determining the quantity of N-acetyl-β-glucosaminidase present in a female biological medium, said quantity being indicia of fertility or pregnancy, comprising contacting said medium at an acidic pH with an N-acetyl-β-d-glucosaminide that reacts in the presence of said glucosaminidase at said acidic pH to form a reaction product that has a distinct color at a predetermined pH and, after said reaction product has formed, establishing said predetermined pH.

10. The method of claim 9 wherein the female biological medium is saliva.

11. The method of claim 9 wherein the N-acetyl-β-d-glucosaminide is a phenolic derivative of N-acetyl-β-d-glucosamine, the reaction product is a phenol and said predetermined pH is an alkaline pH.

12. The method of clam 11 wherein the acidic pH is in the range of 4–5 and the alkaline pH is in the range of 8–11.

13. The method of claim 12 wherein the alkaline pH is in the range of 9–11.

14. The method of claim 12 wherein the phenolic derivative of N-acetyl-β-d-glucosamine is selected from the group consisting of 1-(p-nitrocatechol)-N-acetyl-β-d-glucosaminide, 2-(p-nitrocatechol-N-acetyl-β-d-glucosaminide, 3,3-bis(p-hydroxyphenyl)phthalid-N-acetyl-β-d-glucosaminide, 3-amino-4-nitrophenyl-N-acetyl-β-d-glucosaminide, 2-methyl-4-nitrophenyl-N-acetyl-β-d-glucosaminide, 3-methyl-4-nitrophenyl-N-acetyl-β-d-glucosaminide, 3-nitro-2,4,6-trimethylphenyl-N-acetyl-β-d-glucosaminide, 2-acetylamino-4-nitrophenyl-N-acetyl-β-d-glucosaminide, 3-nitro-4-methoxyphenyl-N-acetyl-β-d-glucosaminide, 3-nitro-4-acetylphenyl-N-acetyl-β-d-glucosaminide, 3-nitro-4-methylphenyl-N-acetyl-β-d-glucosaminide, 2-methoxy-4-nitrophenyl-N-acetyl-β-d-glucosaminide, m-nitrophenyl-N-acetyl-β-d-glucosaminide, 2,4-dinitrophenyl-N-acetyl-β-d-glucosaminide, 2,6-dinitrophenyl-N-acetyl-β-d-glucosaminide, 2,5-dinitrophenyl-N-acetyl-β-d-glucosaminide, o-nitro phenyl-N-acetyl-β-d-glucosaminide, and 2-amino-4-nitrophenyl-N-acetyl-β-d-glucosaminide.

15. The method of claim 12 wherein the acidic pH is maintained by contacting said medium with said N-acetyl-β-d-glucosaminide in the presence of a buffer compounded from sodium citrate and citric acid and said alkaline pH is established by adding a sodium glycinate buffer to the reaction mixture.

16. The method of claim 9 wherein the medium is contacted with the N-acetyl-β-d-glucosaminide at an acid pH for an incubation period in the range of 20 to 40 minutes.

17. The method of claim 9 wherein the female biological medium is saliva, the acidic pH is in the range of 4–5 and is maintained by contacting said medium with said N-acetyl-β-d-glucosaminide in the presence of a buffer compounded from sodium citrate and citric acid, the N-acetyl-β-d-glucosaminide is selected from the group consisting of p-nitrophenyl-N-acetyl-β-d-glucosaminide and 3,3-bis(p-hydroxyphenyl)phthalid-N-acetyl-β-d-glucosaminide, the predetermined pH is in the range of 9–11 and is established by adding a sodium glycinate buffer to the reaction mixture, and the medium is contacted with the N-acetyl-β-d-glucosaminide at said acidic pH for 20 to 40 minutes.

* * * * *